United States Patent [19]

Rose

[11] 4,145,548

[45] Mar. 20, 1979

[54] METHOD FOR THE PRODUCTION OF 5-NITROSO-2,4,6-TRIAMINOPYRIMIDINE

[75] Inventor: David Rose, Hilden, Fed. Rep. of Germany

[73] Assignee: Henkel Kommanditgesellschaft auf Aktien, Dusseldorf-Holthausen, Fed. Rep. of Germany

[21] Appl. No.: 850,287

[22] Filed: Nov. 10, 1977

[30] Foreign Application Priority Data

Nov. 12, 1976 [DE] Fed. Rep. of Germany ....... 2651794

[51] Int. Cl.$^2$ ............................................ C07D 239/50
[52] U.S. Cl. .................................................. 544/323
[58] Field of Search ................. 260/256.4 N; 544/323

[56] References Cited

PUBLICATIONS

Sato et al., *Chemical Abstracts,* vol. 47 (1953), 5946f.

*Primary Examiner*—Paul M. Coughlan, Jr.
*Attorney, Agent, or Firm*—Hammond & Littell

[57] ABSTRACT

An improved process for the production of 5-nitroso-2,4,6-triaminopyrimidine comprising boiling an arbitrary guanidine salt, dissolved in an aliphatic lower alcohol, with malonic acid dinitrile in the presence of a base, cooling and acid adjusting the reaction mixture and adding water thereto, treating the aqueous acid-adjusted reaction mixture with nitrous acid and recovering 5-nitro-2,4,6-triaminopyrimidine without isolation of intermediately formed products.

11 Claims, No Drawings

METHOD FOR THE PRODUCTION OF 5-NITROSO-2,4,6-TRIAMINOPYRIMIDINE

BACKGROUND OF THE INVENTION 5-nitroso-2,4,6-triaminopyrimidine has up to now been produced by a method such as is described by Sato et al, in J. Chem. Soc., Japan, Pure Chem. Sect., 72, 866–8 (1951). In accordance with this method, guanidine nitrate is first agitated for four hours with sodium in a methanolic solution, the precipitated sodium nitrate is filtered off and the methanol is removed in vacuo at 50° C. The guanidine obtained is dissolved in ethanol. A solution of malonic acid dinitrile in butanol is added to this ethanolic guanidine solution. The 2,4,6-triaminopyrimidine, precipitated after brisk reaction, is filtered off and washed several times with ethanol. The 5-nitroso-2,4,6-triaminopyrimidine is obtained by treating 2,4,6-triaminopyrimidine with sodium nitrite in dilute acetic acid and filtered off the desired 5-nitroso-2,4,6-triaminopyridmine from the reaction mixture. This method requires isolation of the two intermediate and the final reaction product and is too complicated and too expensive for commercial production.

OBJECTS OF THE INVENTION

An object of the present invention is the development of a commercial method to produce 5-nitroso-2,4,6-triaminopyrimidine in commercial quantities exceeding those required for purely scientific purposes which did not have the disadvantages of the known method, without impairing the yield and quality of the product.

Another object of the present invention is the development of an improved process for the production of 5-nitroso-2,4,6-triaminopyrimidine consisting essentially of the steps of:

(1) introducing an arbitrary guanidine salt into a water-miscible lower aliphatic alcohol, (2) adding a basic reacting compound in a stoichiometric excess and malonic acid dinitrile thereto, (3) heating the reaction mixture to reflux under normal pressure for from 30 minutes to six hours, (4) cooling the reaction mixture to from 20° C. to 50° C., (5) adjusting the reaction mixture to an acid pH with at least a stoichiometric excess of an acid, (6) adding water to the acid-adjusted reaction mixture in an amount of from 0.5 to 4 times the volume of the acid-adjusted reaction mixture, (7) reacting said acid-adjusted aqueous reaction mixture with nitrous acid under nitrosating conditions, and (8) recovering said 5-nitroso-2,4,6-triaminopyrimidine without isolation of any intermediately formed products.

These and other objects of the invention will become more apparent as the description thereof proceeds.

DESCRIPTION OF THE INVENTION

The present invention provides a method of producing 5-nitroso-2,4,6-triaminopyrimidine in a commercially efficient manner by boiling an arbitrary guanidine salt, introduced in an aliphatic water-miscible alcohol having 1 to 4 carbon atoms in the molecule, with malonic acid dinitrile for one-half to six hours at normal pressure in the presence of a basically reacting compound, acid-adjusting the reaction mixture with acetic acid after cooling to 20° C. to 50° C., adding a quantity of water in the ratio of 0.5:1 to 4:1 relative to the mixture, treating the reaction mixture with nitrous acid, and working up the reaction product in a known manner, the reaction being carried out in one processing step without isolating the intermediate products.

More particularly, the present invention relates to an improved process for the production of 5-nitroso-2,4,6-triaminopyrimidine consisting essentially of the steps of:

(1) introducing an arbitrary guanidine salt into a water-miscible lower aliphatic alcohol, (2) adding a basic reacting compound in a stoichiometric excess and malonic acid dinitrile thereto, (3) heating the reaction mixture to reflux under normal pressure for from 30 minutes to six hours, (4) cooling the reaction mixture to from 20° C. to 50° C., (5) adjusting the reaction mixture to an acid pH with at least a stoichiometric excess of an acid, (6) adding water to the acid-adjusted reaction mixture in an amount of from 0.5 to 4 times the volume of the acid-adjusted reaction mixture, (7) reacting said acid-adjusted aqueous reaction mixture with nitrous acid under nitrosating conditions, and (8) recovering said 5-nitroso-2,4,6-triaminopyrimidine without isolation of any intermediately formed products.

The starting compound utilized in the present invention is an arbitrary guanidine salt. The acidic anion is not important since, under the reaction conditions in the presence of a basic compound, the free guanidine is formed which is readily soluble in water-miscible lower aliphatic alcohols. An arbitrary guanidine salt, such as nitrate, sulfate, hydrochloride, phosphate, and acetate, can be used as the starting material without impairing the method. By way of example, alkali metal hydroxides, alkali metal hydrides and alkali metal lower alkanolates, as well as calcium hydroxide and calcium hydride, such as sodium hydroxide, potassium hydroxide, lithium hydroxide, calcium hydroxide, sodium hydride, calcium hydride, lithium hydride, $C_1$–$C_4$ alkanolates of the alkali metals, such as sodium, potassium and lithium, and many others can be used as the basically reacting compound. Suitable alcoholic solvents are preferably water-miscible alkanols, such as methanol, ethanol, n-propanol, isopropanol, n-butanol, isobutanol and tert. butanol. Ethanol and isopropanol are preferably used. The malonic acid dinitrile is employed in about equimolar amounts with respect to the guanidine salt.

While the process is designed to utilize an arbitrary guanidine salt as a starting material because of the economy of the same, it is also possible to start with guanidine per se.

When boiling under reflux, the condensation of guanidine and malonic acid dinitrile requires a reaction time from one-half to six hours according to the nature of the alcohol used and the basically reacting compound. The average reaction period is approximately three hours. The reaction time can be shortened when heating is effected under pressure.

After the reaction is completed, the reaction mixture is cooled to a temperature between 20° C. and 50° C. and adjusted to the acid side by the addition of an aqueous strong mineral acid or strong organic acid, such as hydrochloric acid or acetic acid. Sufficient acid is added whereby a stoichiometric excess is present over that required to neutralize the basic reacting compound and the 2,4,6-triaminopyrimidine produced so that the reaction mixture is distinctly acid with a pH of preferably below 5.

An essential feature of the method of the present invention is the addition of large quantities of water before and during the nitrosating treatment with nitrous acid. This increases the yield of the 5-nitroso-2,4,6-triaminopyrimidine and facilitates the working-up of the reaction mixture. The quantity of water added is to be between 0.5:1 and 4:1 relative to the reaction mixture. The quantity of water added is generally limited to a ratio of from 0.5:1 to 2:1 in order to avoid the use of oversize reaction vessels which would render the method unmanageable. This possibility of increasing the yield and promoting the working-up of the product by adding a large quantity of water was not to be anticipated from the knowledge of the prior art.

The reaction mixture acid-adjusted with acetic acid is treated with nitrous acid by means of in situ formation from a nitrite compound such as sodium nitrite in a manner known per se. Preferably the acid-adjusted aqueous mixture and sodium nitrite are agitated for a period of time then heated slightly in order to complete the nitrosation reaction.

After cooling to room temperature, the precipitated 5-nitroso-2,4,6-triaminopyrimidine can be recovered by filtration, water washing and drying. Excellent yields of the desired product are obtained.

The 5-nitroso-2,4,6-triaminopyrimidine obtained in accordance with the invention constitutes an important intermediate product for a wide variety of compounds. Thus, 2,4,7-triamino-6-phenyl-pteridine, which is important as a diuretic, is obtained by reaction with benzyl cyanide. 2,4,5,6-tetraaminopyrimidine, which is suitable as a developer component for oxidation hair dyes and is physiologically harmless, can be obtained from 5-nitroso-2,4,6-triaminopyrimidine by catalytic hydrogenation.

The present invention will now be further described by means of the following Example which is not to be deemed limitative in any manner.

EXAMPLE

Production of 5-nitroso-2,4,6-triaminopyrimidine

The entire reaction was carried out under a nitrogen atmosphere.

6.48 kg of guanidine hydrochloride were dissolved in 30 liters of ethanol in a boiler provided with a heater, cooler and a reflux condenser. 6.0 kg of sodium methylate were then added, the temperature being kept below 25° C. A solution of 4.5 kg of malonic acid dinitrile in 30 liters of ethanol was subsequently added at 20° C. during the course of one hour.

The reaction mixture was then boiled for three hours under reflux (approximately 80° C.) and then the mixture was cooled to 20° C. to 25° C. 14.6 kg of an acetic acid/water mixture (1:1) were added to the mixture during the course of one hour at a temperature maintained below 25° C., and then 55 liters of water were added. A solution of 4.73 kg of sodium nitrite in 9 liters of water was then added rapidly and the mixture was agitated for a further two hours. The mixture was then heated slowly to 50° C. and was agitated for two hours at this temperature. After cooling to 20° C., the precipitate obtained was filtered off and re-washed with warm water. The wet product can be used as such for further processing, otherwise the compound was dried in a conventional manner. The yield of raspberry-red 5-nitroso-2,4,6-triaminopyrimidine having a melting point of >300° C. was 9.673 kg corresponding to 93% of the theoretical yield.

The preceding specific embodiment is illustrative of the practice of the invention. It is to be understood, however, that other expedients known to those skilled in the art or disclosed herein, may be employed without departing from the spirit of the invention or the scope of the appended claims.

We claim:

1. An improved process for the production of 5-nitroso-2,4,6-triaminopyrimidine consisting essentially of the steps of:
   (1) introducing an arbitrary guanidine salt into a water-miscible lower aliphatic alcohol,
   (2) adding a basic reacting compound in a stoichiometric excess and malonic acid dinitrile thereto,
   (3) heating the reaction mixture to reflux under normal pressure for from 30 minutes to six hours,
   (4) cooling the reaction mixture to from 20° C. to 50° C.,
   (5) adjusting the reaction mixture to an acid pH with at least a stoichiometric excess of an acid,
   (6) adding water to the acid-adjusted reaction mixture in an amount of from 0.5 to 4 times the volume of the acid-adjusted reaction mixture,
   (7) reacting said acid-adjusted aqueous reaction mixture with nitrous acid under nitrosating conditions, and
   (8) recovering said 5-nitroso-2,4,6-triaminopyrimidine without isolation of any intermediately formed products.

2. The process of claim 1 wherein said arbitrary guanidine salt is the salt selected from the group consisting of the nitrate, the sulfate, the hydrochloride, the phosphate and the acetate.

3. The process of claim 1 wherein said water-miscible lower aliphatic alcohol is an alkanol having from 1 to 4 carbon atoms.

4. The process of claim 3 wherein said alkanol is ethanol.

5. The process of claim 3 wherein said alkanol is isopropanol.

6. The process of claim 1 wherein said basic reacting compound is a member selected from the group consisting of alkali metal hydroxides, alkali metal hydrides, alkali metal alkanolates of alkanols having 1 to 4 carbon atoms, calcium hydroxide and calcium hydride.

7. The process of claim 1 wherein said basic reacting compound is sodium methylate.

8. The process of claim 1 wherein said reaction mixture is adjusted to an acid pH of below 5.

9. The process of claim 1 wherein the amount of water added is from 0.5 to 2 times the volume of the acid-adjusted reaction mixture.

10. The process of claim 1 wherein said nitrous acid is formed in situ.

11. The process of claim 1 wherein said acid-adjusted aqueous reaction mixture is reacted with sodium nitrite to form nitrous acid in situ.

* * * * *